United States Patent [19]
Fletcher

[11] Patent Number: 5,267,996
[45] Date of Patent: Dec. 7, 1993

[54] LASER SURGERY ASPIRATION APPARATUS AND TECHNIQUE

[75] Inventor: Henry H. Fletcher, Cupertino, Calif.

[73] Assignee: Laserscope, San Jose, Calif.

[21] Appl. No.: 666,095

[22] Filed: Mar. 7, 1991

Related U.S. Application Data

[63] Continuation-in-part of Ser. No. 614,358, Nov. 15, 1990, abandoned.

[51] Int. Cl.[5] .............................................. A61B 17/36
[52] U.S. Cl. ........................................ 606/17; 604/35; 606/16
[58] Field of Search .......................... 606/3, 7, 10–17, 606/27, 28, 32, 41, 45, 48, 46; 128/4, 4 A, 6; 604/22, 35

[56] References Cited

U.S. PATENT DOCUMENTS

| 4,369,788 | 1/1983 | Goald . | |
|---|---|---|---|
| 4,545,374 | 10/1985 | Jacobson . | |
| 4,580,557 | 8/1983 | Hertzmann . | |
| 4,592,353 | 6/1986 | Daikuzono | 606/17 X |
| 4,678,459 | 7/1987 | Onik et al. . | |
| 4,694,828 | 1/1987 | Eichenbaum . | |
| 4,722,337 | 2/1988 | Losch et al. . | |
| 4,725,115 | 2/1988 | Beasley . | |
| 4,736,732 | 4/1988 | Shimonaka | 128/4 A |
| 4,740,047 | 4/1988 | Abe et al. | 128/4 X |
| 4,832,024 | 5/1989 | Boussignac et al. | 606/15 X |
| 4,881,523 | 11/1989 | Heckele | 128/4 |
| 4,932,989 | 6/1990 | Presby . | |
| 4,960,419 | 10/1990 | Rosenberg | 606/45 |
| 4,986,825 | 1/1991 | Bays et al. | 604/22 |

FOREIGN PATENT DOCUMENTS 3232007  3/1983  Fed. Rep. of Germany ........ 606/16

OTHER PUBLICATIONS

Hijikata S., Yamagishi M., Nakayama T., Oomori K., "Percutaneous Diskectomy: A New Treatment for Lumbar Disk Herniation", J. Toden Hosp., 1975; 5:5–13.
Ascher P. W., Choy, D. S., Yuri H., "Percutaneous Nucleus Pulposus Denaturation and Vaporization of Protruded Discs", Abstract #202, p. 48, Lasers in Surgery and Medicine, Supplement 1, 1989.
Ascher P. W., "Laser Trends in Minimally Invasive Treatment: Atherosclerosis, Disc Herniations", Section 2. presented at the Biomedical Optics Conference of SPIE, Los Angeles, Jan. 26, 1990.
Hashimoto, D. et al., "A Lateral Radiation Probe In YAG Laser Therapy", Gastrointestinal Endoscopy, vol. 32, No. 2, (1986) pp. 124–125.

Primary Examiner—Peter A. Aschenbrenner
Attorney, Agent, or Firm—Skjerven, Morrill MacPherson, Franklin & Friel

[57] ABSTRACT

An apparatus and method of aspirating vapors during laser surgery couples a vaporizing device with a source of vacuum. The apparatus includes an aspiration connector insertable into the vaporizing device and coupled to an optical waveguide disposed along a bore of the device. An aspiration pathway extends along with the optical waveguide in the bore of the vaporizing device forming a compact single passageway vaporizing device with aspiration capability. Vacuum control points are provided along the aspiration pathway to adjust the vacuum at an end where the vapors are formed.

4 Claims, 7 Drawing Sheets

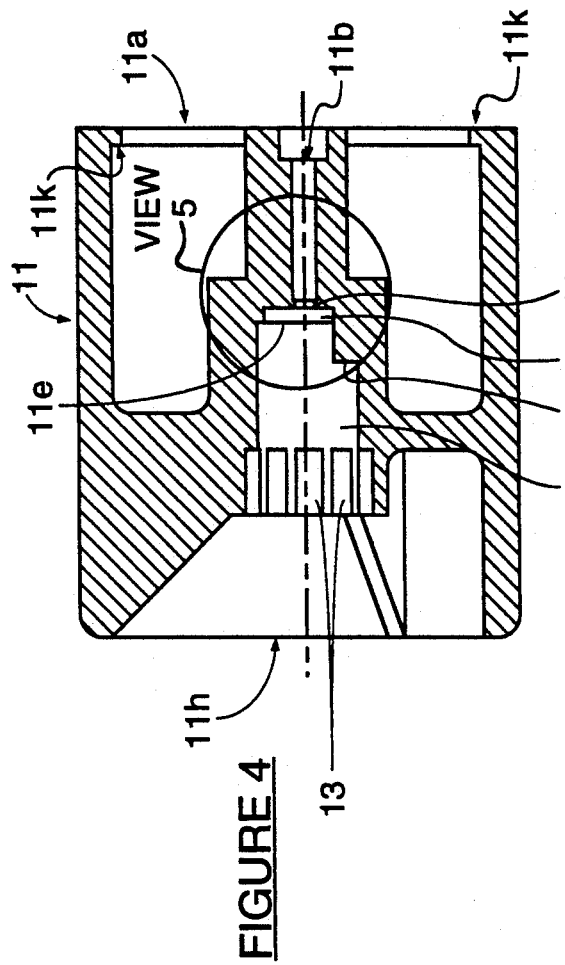
FIGURE 4
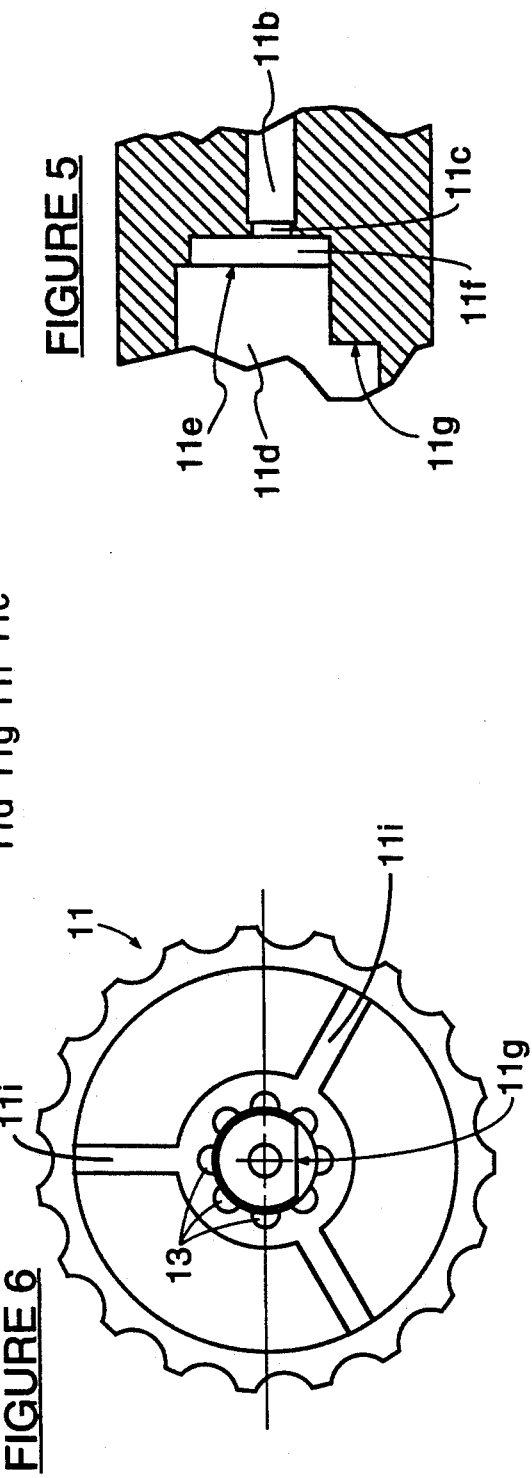

LASER SURGERY ASPIRATION APPARATUS AND TECHNIQUE

CROSS REFERENCE TO RELATED APPLICATION

This application is a continuation-in-part of copending U.S. patent application Ser. No. 07/614,358, filed Nov. 15, 1990.

BACKGROUND

1. Field of the Invention

This invention relates to aspirating vaporized material and in particular, smoke, steam and fine particulates of vaporized material during surgery and treatment.

2. Description of the Prior Art

U.S. Pat. No. 4,678,459 to Onik et al. discloses a percutaneous diskeotomy system (for surgery on the disks in the human back) having an irrigation device and vacuum device for aspirating tissue fragments severed by a guillotine cutting device. The system disclosed by Onik et al. provides irrigation fluid and vacuum for moving tissue fragments internally along the system for removal. The irrigation pathways are relatively large in diameter to accommodate the tissue fragments and irrigation fluids. Onik et al. does not disclose or suggest using a laser to vaporize tissue or aspirating vaporized tissue.

U.S. Pat. No. 4,694,828 to Eichenbaum discloses a laser system including a handpiece and nose cone assembly having mating passageways for aspiration and irrigation. The nose cone assembly comprises an outer housing, an inner housing and an aspiration tube located inside the inner housing, all with coaxially aligned lateral openings defining a photovaporization chamber. Eichenbaum discloses that tissue is aspirated into the chamber where it is vaporized and conducted along the aspiration tube. The aspiration and irrigation passageways are separate from and adjacent to the optical fiber passageway, thus resulting in a fairly large diameter device to be inserted into the body. Eichenbaum does not disclose or suggest aspirating vaporized tissue along essentially the same passageway that the optical fiber is disposed.

There is a need therefore for a relatively simple and compact (small diameter) device for aspirating vaporized material, thereby decreasing the overall diameter of the portion of the device inserted into the body.

SUMMARY OF THE INVENTION

The present invention combines with instrumentation, such as devices for vaporizing material (i.e., human tissue) which use an optical guiding means for transmitting energy to the surgical site, and provides an aspiration passageway for the vaporized material that is essentially the same as the passageway in which the optical guiding means is disposed. Since the material is vaporized into smoke, steam and fine particulates, irrigation fluids and irrigation passageways are not necessary. A vaporizing device incorporating the invention has an overall compact (i.e., is of small diameter) and relatively simple structure compared to the prior art devices because the aspiration means according to the invention uses an existing passageway in the instrument for aspiration. The invention is therefore particularly adaptable to devices which vaporize material using laser energy transmitted along optical fibers for laser surgery and treatment. Applicable medical treatments which use a vaporizing device and would use an aspiration means according to the invention include arthroscopy, orthopedics, laparoscopy, such as cholecystectomy, adhesiolysis; carpal tunnel release; otorhinolaryngology, such as excision of granuloma, polyps and ranula, and tonsillectomy; gynecology, such as ablation of endometriosis, intrauterine adhesiolysis, and uterosacral ligament transection; neurosurgery, such as excision, coagulation and vaporization of firm textured tumors including meningioma, hemangioma and neuroma and percutaneous lumbar diskectomy; and treatment of varicose veins.

According to the invention, a method and apparatus are disclosed for aspirating vaporized material. "Vaporized material" and "vaporization" as used herein include smoke, particles, and drops of liquid and the creation of the same. One apparatus for aspirating such vapors is coupled with a vaporizing device and comprises means for aspirating insertable in the vaporizing device, the means for aspirating being coupled to an optical guiding means of the vaporizing device, thereby disposing the optical guiding means essentially along an aspiration pathway through the device.

One method of aspirating vapors, such as smoke, steam and fine particulates, through a vaporizing device comprises providing a vacuum source near one end of the vaporizing device through a passageway of the device through which an optical guiding means is disposed; and providing air (or other fluid) along the passageway, thereby controlling the vacuum pressure at another end of the vaporizing device, where vapors are drawn into the device.

The apparatus and method according to the invention decrease the diameter of the vaporizing device over the prior art multiple passageway devices by providing an aspiration passageway within the same bore of the device where the optical guiding means is disposed.

BRIEF DESCRIPTION OF THE FIGURES

FIG. 4 illustrates the probe portion of the housing in a cross-sectional view along the length of the housing.

FIG. 5 illustrates an enlarged view of one part of FIG. 4.

FIG. 6 illustrates a cross-sectional view of the probe portion of the housing along section 6—6 of FIG. 3.

DETAILED DESCRIPTION OF THE INVENTION

The apparatus for aspirating vapors according to the invention advantageously couples to different types of instrumentation, such as to devices which use light energy to vaporize, coagulate and/or sever material, such as tissue. A vaporizing device typically uses an optical guiding means for transmitting light energy to a target site. The apparatus according to the invention provides an aspiration means for removing the vaporized debris from the target site.

One embodiment of the apparatus couples to an instrument of copending and commonly owned U.S. patent application Ser. No. 07/614,358, filed Nov. 15, 1990, entitled "Instrumentation For Directing Light at An Angle" by Fletcher et al., hereby incorporated by reference, which is illustrated in part in FIGS. 1-5 and 9 herein. The instrument vaporizes tissue and cartilage with light energy transmitted along an optical fiber. In particular, the instrument of FIG. 1 directs light at an angle to the longitudinal axis of the optical guiding means. The invention is adaptable to other instruments requiring aspiration capability, for example instruments using other light guiding means, such as hollow optical waveguides, or instruments which direct light in the direction of the longitudinal axis of the optical guiding means without going beyond the intended scope of the invention.

Figure 1:
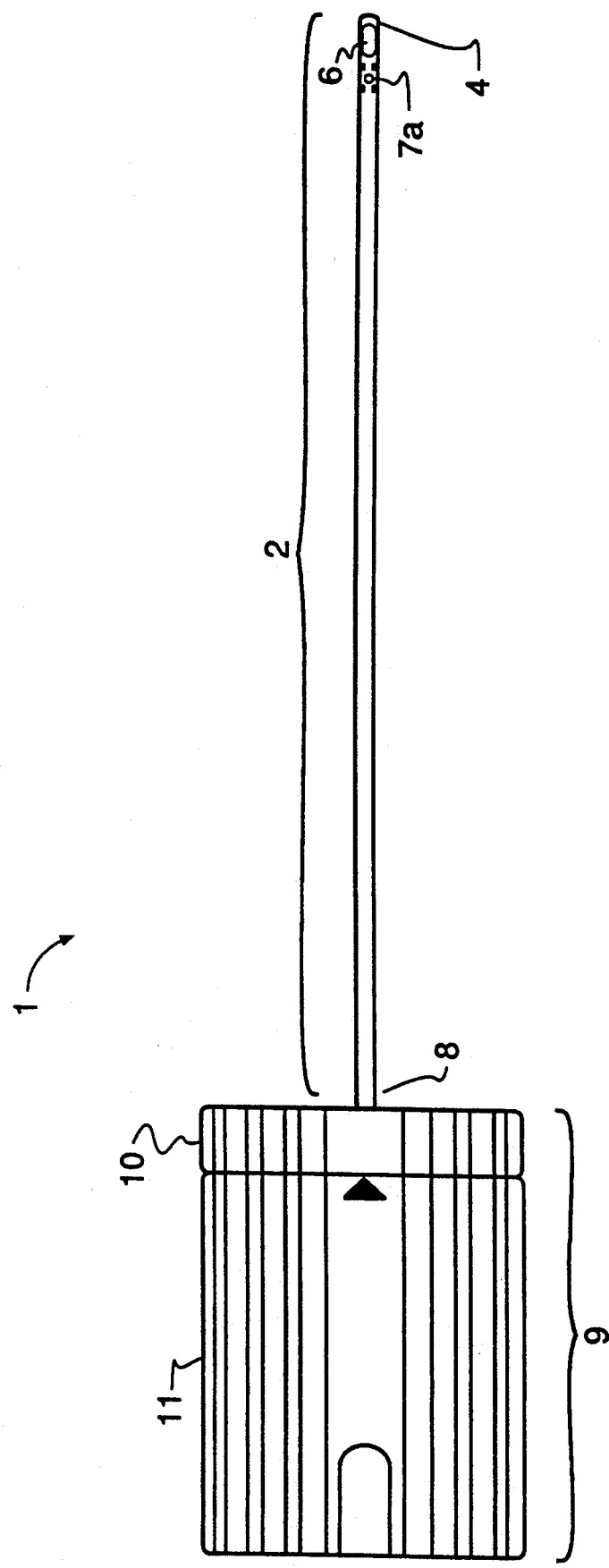
FIG. 1 illustrates the cylindrical probe and housing according to the invention.

In FIG. 1, instrument 1 is a vaporizing device which has many uses in medical treatment. Instrument 1 can be used for example, in diskectomy surgery (i.e., repair of inter-vertebral disks) and comprises a long cylindrical probe 2, which introduces an optical guiding means into a patient. The optical guiding means disposed along a bore of cylindrical probe 2 and housing 9 transmits light (such as laser light) to the area of interest, such as the nucleus of the patient's vertebral disk. An end 4 of the cylindrical probe 2 is inserted through a conventional surgical cannula (not shown), having an inside diameter larger than the outside diameter of probe 2, to the area of interest. The large diameter cannula and other insertion instrumentation used in percutaneous diskectomy, for example, is described in more detail in copending and commonly owned U.S. patent application Ser. No. 07/463,758, filed Jan. 12, 1990, hereby incorporated by reference. End 4 can have different shapes and openings depending on the intended application of the vaporizing device.

In another embodiment, the vaporizing device is used to treat nasal polyps and differs from the device in FIG. 1 at least at end 4 where light exits the device. In this embodiment, the end 4 has a plurality of sharp edges for embedding into the nasal polyp tissue for the treatment.

Figure 2:
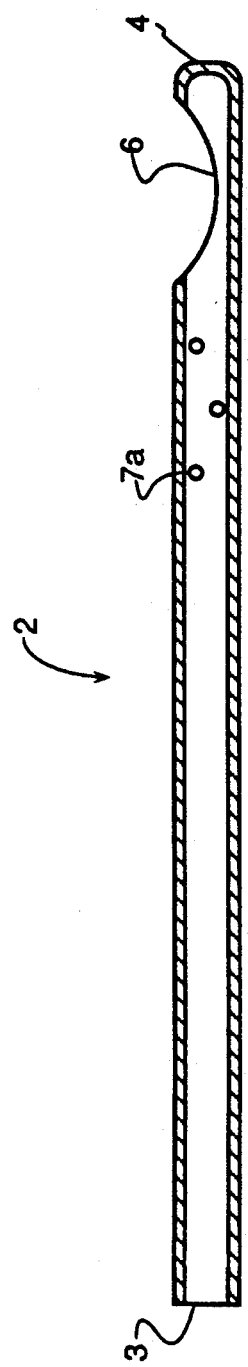
FIG. 2 illustrates a cross-sectional area of one end of the cylindrical probe.

FIG. 2 is an enlarged cross-sectional view of the end 4 and a length of probe 2 according to the embodiment of FIG. 1. The cylindrical probe 2 has an opening, which is a cut-out 6 located in one side of probe 2 near end 4 in this embodiment. This opening is aligned with an end 16 of the optical guiding means which directs light at an angle to the longitudinal axis of the optical guiding means. In another embodiment, end 4 can have an opening which is perpendicular to the sides of the probe 2 to accommodate an optical guiding means which directs light in the direction of the longitudinal axis of the guiding means. The cylindrical probe 2 has a plurality (such as nine) of smoke aspiration holes 7a near the end 4 in the embodiment of FIG. 1. Aspiration holes 7a can vary in number and size, and in one embodiment, are approximately 0.031 inches in diameter and staggered around the perimeter of probe 2 approximately 120° apart. The opening and aspiration holes 7a are continuous with the bore of probe 2.

On the end 8 (see FIG. 1) opposite to the end 4 of the cylindrical probe 2 is a housing 9 of a conventionally molded plastic approximately 1.9 inches long and approximately 1.25 inches in diameter in one embodiment. Housing 9 is readily manipulatable with the finger and thumb of one hand and has a mechanism for limiting (axial or longitudinal) travel (not shown).

Figure 3:
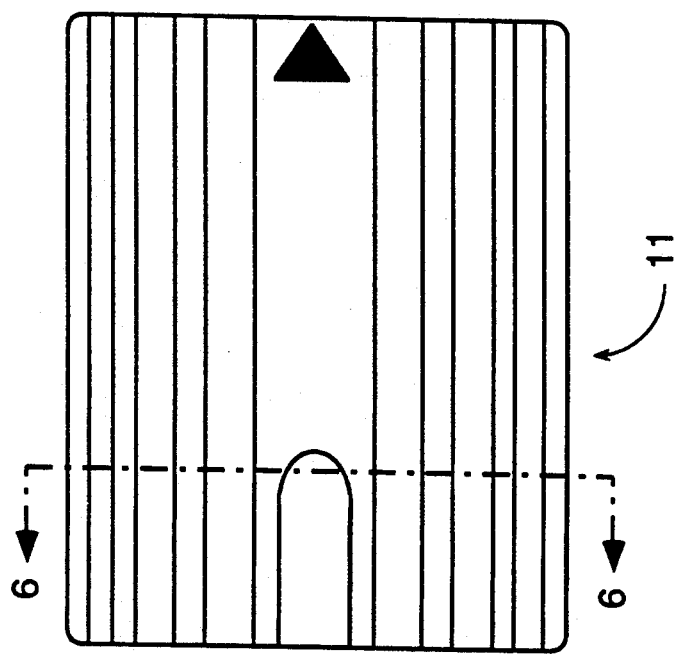
FIG. 3 illustrates the probe portion of the housing according to the invention.

Probe portion 11 of housing 9 is illustrated in FIGS. 3-6. FIG. 3 is a side view of the probe portion 11. FIG. 4 is a cross-sectional view of probe portion 11 taken along the length thereof. FIG. 5 is an enlarged view of a portion of FIG. 4 encircled and labeled with reference numeral 5. FIG. 6 is a cross-sectional view of probe portion 11 taken along line 6—6 of FIG. 3. In one embodiment, probe portion 11 of housing 9 is a cylindrical tube approximately 1.6 inches long having a bore of varying diameters along its length and a plurality of gripping ribs, such as eighteen ribs. The smallest diameter of the bore is sized to accommodate an optical guiding means therethrough and the largest diameter is sized to accommodate the mechanism for limiting travel. One end 11a (see FIG. 4) receives the mechanism for limiting travel. End 11a of probe portion 11 also has probe 2 receiving hole 11b which extends internally approximately halfway along the length of housing 9 and has a slightly larger diameter at end 11a. The other end of probe receiving hole 11b has a neck 11c adjacent to an aspiration connector receiving hole 11d.

Aspiration connector receiving hole 11d has a larger diameter than probe receiving hole 11b for receiving an aspiration connector 12 according to the invention and described in more detail below. Hole 11d has a connector stop 11e adjacent to aspiration hole portion 11f located adjacent to neck 11c and connector stop 11e. FIG. 5 is an enlarged view detailing the portion of probe housing 11 where neck 11c, aspiration hole portion 11f, and connector stop 11e are located.

Hole 11d further includes optional flat step 11g which keys with optional flat step 12g on aspiration connector 12 (described below). A flat step 11g is provided in this embodiment to rotationally key or orient the aspiration connector 12 one certain way. As will be described in more detail below, the aspiration connector 12 is coupled to the optical guiding means 5 before the guiding means is installed in the instrument 1. The end 16 of the optical guiding means must be aligned and oriented a certain way with the cut-out 6 for the light to pass through the cut-out 6 to the target area in this embodiment. Hole 11d terminates in a recessed location in housing 9 near end 11h.

As illustrated in FIG. 4, the opening in probe portion 11 is much wider at end 11h than the hole 11d and extension branches 11i, as illustrated in FIG. 6, connect between end 11h of housing 9 and the hole 11d in one embodiment.

FIG. 6 illustrates, in cross section along line 6—6 of FIG. 3, end 11h of housing 9 and shows scalloped cut-outs 13 along with flat step 11g. Scalloped cut-outs 13 accommodate the shape of scalloped edges 12h of the aspiration connector 12 when connector 12 is inserted.

Figure 7:
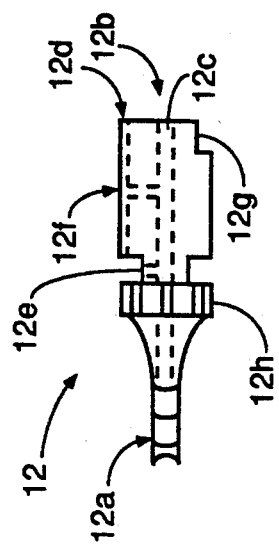
FIG. 7 illustrates a side view of an aspiration connector according to the invention.

Referring to FIG. 7, one embodiment of aspiration connector 12 according to the invention, is cylindrical in shape and has a tubing connector 12a at one end. The tubing connector 12a has a ribbed male fitting, which attaches to aspiration tubing, and a flared neck having scalloped edges 12h. This embodiment of connector 12 is adapted to the vaporizing device of FIG. 1 which directs light at an angle to the longitudinal axis of the optical guiding means. Therefore, in this embodiment connector 12 has the flat step 12g which keys together with the flat step 11g of housing 9 as mentioned above.

An aspiration and fiber receiving bore 12c extends through connector 12. In one embodiment, channels 12e and 12f connect bore 12c to paths leading outside of connector 12. Channel 12e connects with the aspiration system described below. Optional channel 12f is provided for inserting a means for attaching and holding an optical guiding means in place in aspiration connector 12. When an adhesive is used for holding the optical guiding means, it is applied via channel 12f, where adhesive fills the channel and flows into bore 12c to contact the optical guiding means and adhere the optical guiding means to connector 12, thereby blocking bore 12c at channel 12f.

Aspiration connector 12 further includes channel 12d, providing a pathway connecting hole 11f and channel 12e of the aspiration system. The aspiration pathway is diverted from bore 12c along channel 12d to bypass the blockage at position 12f in bore 12c when adhesive is used to hold the optical guiding means in place.

The aspiration system according to the invention is used with vaporization devices to provide an aspiration passageway essentially along the passageway created for the optical guiding means. The apparatus is adapted to be coupled to any vaporizing device to form a compact, single passageway vaporization and aspiration device for laser surgery or other methods of medical treatment.

Figure 8:
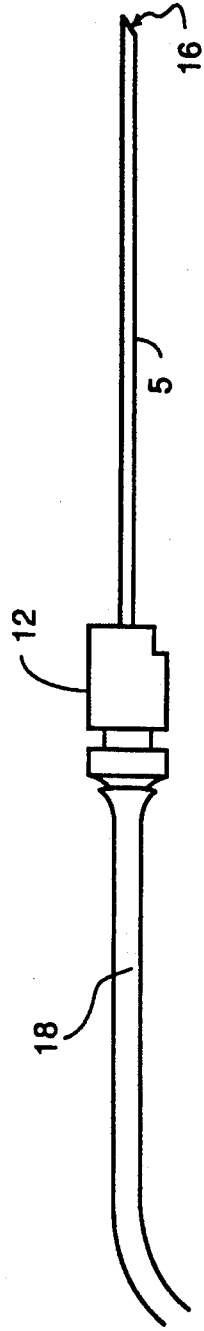
FIG. 8 illustrates the optical fiber attached to an aspiration connector and associated tubing according to the invention.
Figure 9:
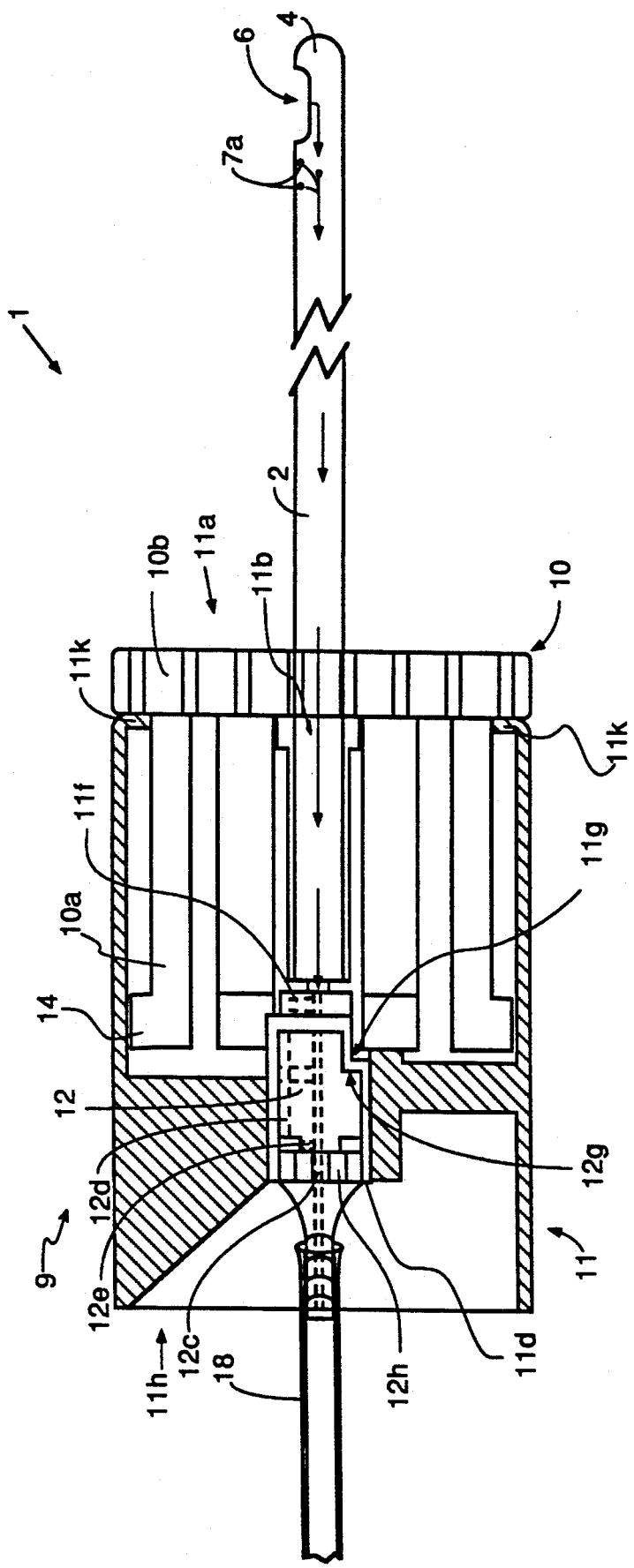
FIG. 9 illustrates the aspiration connector of FIG. 8 installed in the housing.
Figure 10:
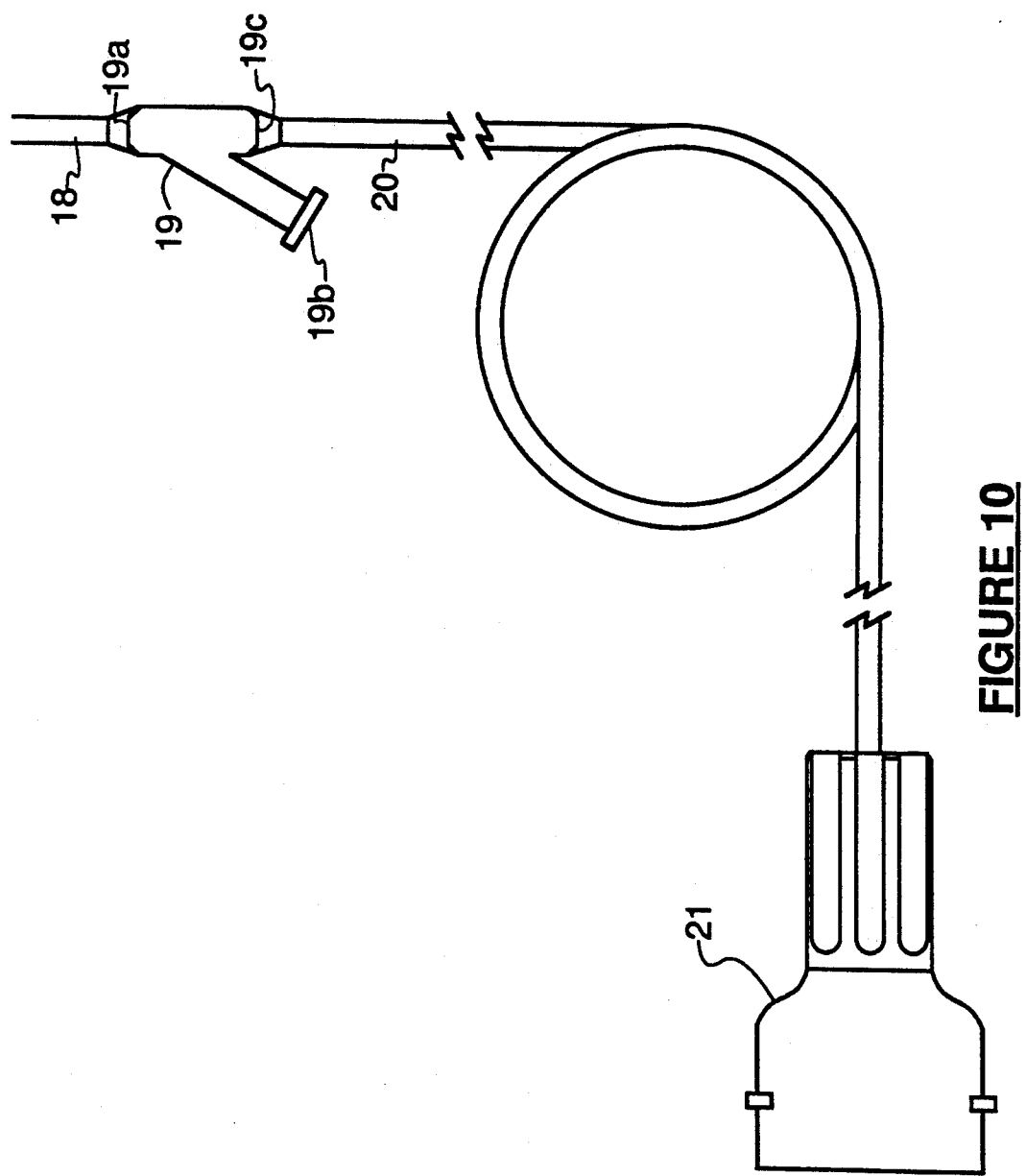
FIG. 10 is a plan view of an aspiration clamp, aspiration tubing and diverter.

Referring to FIG. 8, optical guiding means 5 is inserted through bore 12c of aspiration connector 12 to extend for a distance from one end, while aspiration tubing 18 is installed on tubing receiving end 12a of aspiration connector 12 from the other end. Optical guiding means 5 is disposed in the bore of aspiration tubing 18 to a point where tubing 18 is connected to a diverter 19 as illustrated in FIG. 10 and described further below. According to one embodiment, optical guiding means 5 is permanently installed in receiving bore 12c of aspiration connector 12 with an adhesive, such as a cyanoacrylate, applied via channel 12f, as mentioned above. Aspiration connector 12 and optical guiding means 5 are installed together in housing 9 through end 11h. FIG. 9 illustrates housing 9 assembled with aspiration connector 12, according to the embodiment of FIG. 1. In this embodiment, flat step 12g abuts flat step 11g inside housing 9 thereby automatically orienting aspiration connector 12 to housing 9 both rotationally and axially in a single way. Where a particular orientation is not required, flat steps 12g and 11g are not provided.

According to the embodiment of the vaporizing device illustrated in FIGS. 1 and 2, cylindrical probe 2 is installed from end 11a into probe receiving hole 11b. Cylindrical probe 2 is permanently installed into housing 9 using an adhesive, such as a cyanoacrylate, to hold probe 2 in place in one embodiment. Excess adhesive accumulates in the wider taper at end 11a of probe receiving hole 11b.

When the assembly according to the invention illustrated in FIG. 8 is installed in housing 9, as illustrated in FIG. 9, optical guiding means 5 (not shown in FIG. 9) is inserted first through end 11h to feed through the bore extending from end 11h to end 11a of housing 9 and to feed into cylindrical probe 2. Optical guiding means 5 extends into cylindrical probe 2 for a predetermined distance depending on the length of the cylindrical probe. When aspiration connector 12 is rotationally keyed into aspiration connector receiving hole 11d, as described above, the end 16 of the optical guiding means 5 is aligned with cut-out 6 at the end 4 of cylindrical probe 2. The end 16 of optical guiding means 5 is beveled in this embodiment so that light is directed at an angle off the end 16 from the longitudinal axis of the guiding means 5 through cut-out 6. Therefore, alignment between end 16 and cut-out 6 is critical. Consequently, optical guiding means 5 has a single orientation when installed and bonded into aspiration connector 12 so that when aspiration connector 12 and optical guiding means 5 are installed in housing 9, the orientation of the optical guiding means 5 is set. Aspiration connector 12 can be held in place in housing 9 with adhesive, such as a cyanoacrylate, or mechanically with fasteners or snap coupled, for example.

The mechanism for limiting travel is inserted into probe portion 11 from end 11a to form housing 9 prior to the installation of aspiration connector 12. The means for limiting travel has an opening with a twist locking design to receive and lock onto a connector (not shown) of the large cannula (not shown).

Once the assembled instrument 1 of FIG. 9 is locked onto the large cannula (not shown), the cylindrical probe 2 and optical guide means 5 rotate together clockwise or counterclockwise, but move axially forward and backward in the large cannula only a limited distance determined by the means for limiting travel. The instrument 1 is rotated by rotating probe portion 11 while the mechanism for limiting travel remains stationary and locked to the large cannula. As a safety feature during a lasing operation, for example, the instrument 1 remains locked to the large cannula so that the means for limiting travel prevents damage to the large cannula and the surrounding area by the laser beam. The laser is turned off before the instrument 1 is disconnected from the large cannula to accommodate this safety feature.

As mentioned above, FIG. 8 illustrates that the optical guiding means 5 is attached to aspiration connector 12. The optical guiding means 5 is disposed through the aspiration tubing 18 to where aspiration tubing 18 connects to a Y-shaped diverter 19 having three ports 19a-c as illustrated in FIG. 10, according to one embodiment. The diverter 19 attaches tubing 18 and tubing 20 having optical guiding means 5 disposed therethrough to a laser, according to one embodiment, via clamping connector 21. Clamping connector 21 aligns optical guiding means 5 to the laser output beam as described in detail in commonly owned U.S. Pat. No. 4,722,337 issued to R. Losch et al., Feb. 2, 1988, which is a continuation-in-part of commonly owned U.S. Pat. No. 4,580,557, issued to P. Hertzmann, both incorporated by reference herein. In this embodiment, diverter port 19b is connected to a source of vacuum (not shown), to thereby create the aspiration capability which is combined with the optical guiding means 5 at diverter 19.

In another embodiment, the diverter 19 is replaced and the source of vacuum is provided at the source of light, for example, in the laser system.

One method of aspirating vapors through a vaporizing device comprises providing a source of vacuum near one end of the vaporizing device through the bore essentially containing an optical guiding means; and providing leak passages along the passageway.

According to one embodiment, laser light is directed along optical guiding means 5 in cylindrical probe 2 to a target area, as mentioned above. The laser light vaporizes, coagulates and severs material, and in particular, vaporizes tissue and minimizes blood flow at the target site. Residual smoke, steam, and fine particulates from the vaporized material are removed from the affected area by providing vacuum along the same path as the optical fiber guiding means 5 from diverter 19 (see FIG. 10). The vacuum draws in smoke through the opening at the end 4, such as cut-out 6 and smoke aspiration holes 7a.

As illustrated with arrows in FIG. 9, the smoke follows the aspiration pathway with optical guiding means 5 along the bore of probe 2. The smoke of exits probe 2 at evacuation hole 11f in housing 9 to flow down channel 12d of aspiration connector 12 until channel 12e where the smoke enters bore 12c to be evacuated out tubing 18. The aspiration pathway is the same as the passageway created for optical guiding means 5, but is diverted around the blockage holding the optical guiding means 5 in bore 12c of aspiration connector 12 between hole 11f and channel 12e in one embodiment. The aspiration pathway returns to the same pathway with optical guiding means 5 at channel 12e. The smoke is drawn through port 12a of aspiration connector 12 and through tubing 18 until diverter 19, as illustrated in FIG. 10, where aspirated smoke exits via path 19b connected to a source of vacuum in one embodiment.

Scalloped cut-outs 13 of housing 9 (see FIGS. 4 and 6) and scalloped edges 12h of aspiration connector 12 (see FIG. 7) provide entry passages (fluid leak points) where fluids such as air can enter housing 9 and mix with the smoke in the aspiration path described above. Fluid mixes with smoke and particulates of the vaporized material near channels 12e and 12d and is drawn into channel 12e to be evacuated as described above. The leak passages at scalloped cut-outs 13 and edges 12h create a vacuum pressure gradient along the aspiration pathway such that the vacuum pressure at the opening in probe 2 where the material is vaporized and drawn into probe 2, such as cut-out 6 and aspiration holes 7a, is less than the vacuum pressure at the source of vacuum.

In another embodiment, a predictably low vacuum pressure at the openings in probe 2 can be obtained with a variable aspiration control valve to adjust the amount of fluid leaking in at the leak passages. When the invention is used in arthroscopy procedures, for example, tissue fragments are suspended in a moving saline solution. The variable aspiration control valve adjusts the vacuum pressure for drawing the moving tissue fragments toward the vaporizing source for vaporization and aspiration through the device. During this procedure, some saline solution is aspirated with the vapors and the variable aspiration control valve adjusts the vacuum pressure for aspirating such fluids.

While particular embodiments of the present invention have been shown and described, it will be obvious to those skilled in the art that changes and modifications may be made without departing from this invention in its broader aspects and, therefore, the appended claims are to encompass within their scope all such changes and modifications as fall within the true spirit and scope of this invention.

I claim:

1. An aspiration connector for coupling to a vaporizing device and aspirating vapors generated by said device comprising:

a body defining an aspiration bore aligned with a bore in said vaporizing device when said aspiration connector is coupled with said vaporizing device;

said body further defining an aspiration port at one end for connecting to a source of vacuum having vacuum pressure;

said body further defining intermediate channels along a length of said aspiration connector, at least one of said channels interconnecting the others of said channels, the other channels communicating with said aspiration bore to form an aspiration pathway through said aspiration connector in said device; and means for providing a vacuum pressure gradient along said aspiration pathway such that the vacuum pressure at an end where said vapors are generated is less than the vacuum pressure at said one end of said aspiration connector.

2. The aspiration connector according to claim 1, wherein said means for providing said vacuum pressure gradient comprises leak passages near said one end communicating with at least one of said intermediate channels and said aspiration pathway.

3. The aspiration connector according to claim 1, wherein said vaporizing device comprises:

a probe with an opening near one end and defining a bore;

a housing attached to an opposite end of said probe and defining a bore aligned with the bore of said probe, said aspiration connector insertable in said housing, said bores aligned with said aspiration pathway; and an optical guiding means disposed through said bores and along said aspiration pathway.

4. The aspiration connector according to claim 3, wherein said optical guiding means is disposed through said aspiration bore and exits said aspiration connector through said aspiration port at said one end and through an opposite end of said aspiration connector aligned with said bores.

* * * * *